(12) United States Patent
Hall et al.

(10) Patent No.: US 9,380,992 B2
(45) Date of Patent: Jul. 5, 2016

(54) METHOD AND APPARATUS FOR MEASURING FLOW IN MULTI-DIMENSIONAL ULTRASOUND

(75) Inventors: Anne Lindsay Hall, New Berlin, WI (US); Todor Sheljaskow, Kenosha, WI (US)

(73) Assignee: General Electric Company, Schenectady, NY (US)

( * ) Notice: Subject to any disclaimer, the term of this patent is extended or adjusted under 35 U.S.C. 154(b) by 1790 days.

(21) Appl. No.: 11/731,283

(22) Filed: Mar. 30, 2007

(65) Prior Publication Data

US 2008/0242996 A1 Oct. 2, 2008

(51) Int. Cl.
| | |
|---|---|
| A61B 8/00 | (2006.01) |
| A61B 8/06 | (2006.01) |
| A61B 8/13 | (2006.01) |
| G01S 15/89 | (2006.01) |

(52) U.S. Cl.
CPC ... *A61B 8/00* (2013.01); *A61B 8/06* (2013.01); *A61B 8/13* (2013.01); *G01S 15/8915* (2013.01); *G01S 15/8984* (2013.01); *A61B 8/4472* (2013.01)

(58) Field of Classification Search
USPC .......................................... 600/443, 455, 454
See application file for complete search history.

(56) References Cited

U.S. PATENT DOCUMENTS

| | | | | |
|---|---|---|---|---|
| 4,830,015 | A * | 5/1989 | Okazaki ........................ | 600/442 |
| 5,398,216 | A   | 3/1995 | Hall et al. | |
| 5,409,010 | A * | 4/1995 | Beach et al. .................. | 600/455 |
| 5,421,333 | A * | 6/1995 | Takamizawa et al. ........ | 600/447 |
| 5,454,372 | A   | 10/1995 | Banjanin et al. | |
| 5,465,722 | A * | 11/1995 | Fort et al. ...................... | 600/447 |
| 5,522,393 | A * | 6/1996 | Phillips et al. ................ | 600/455 |
| 5,528,302 | A * | 6/1996 | Basoglu et al. ............... | 348/442 |
| 5,769,079 | A * | 6/1998 | Hossack ........................ | 600/454 |
| 6,071,242 | A * | 6/2000 | Lin ................................ | 600/456 |
| 6,530,887 | B1 * | 3/2003 | Gilbert et al. ................. | 600/459 |
| 6,629,929 | B1 * | 10/2003 | Jago et al. ..................... | 600/447 |
| 2002/0035328 | A1 * | 3/2002 | Roundhill et al. ............ | 600/443 |
| 2007/0083099 | A1 * | 4/2007 | Henderson et al. ........... | 600/407 |

OTHER PUBLICATIONS

Kripfgans, O et al, Vector Doppler Imaging of a Spinning Disc Ultrasound Doppler Phantom, Ultrasound Med Bio 2006, 32(7), pp. 1037-1046.

E. Shrank, D.J. Phillips, W.E. Moritz and D.E. Strandness, Jr. "*A Triangulation Method for the Quantitative Measurement of Arterial blood Velocity Magnitude and Direction in Humans*"; Ultrasound In Med. & Biol., vol. 18, No. 5, pp. 499-509, 1990.

* cited by examiner

*Primary Examiner* — Bo J Peng
(74) *Attorney, Agent, or Firm* — Dean D. Small; The Small Patent Law Group, LLC

(57) ABSTRACT

A method and system are provided for estimating velocity of flow within an ultrasound dataset. A sample volume gate is defined on a two-dimensional (2D) image. The 2D image is based on an ultrasonic dataset. Spectral Doppler velocity estimates of flow are detected within the sample volume gate in first and second dimensions that are orthogonal with respect to each other. A true velocity estimate of the flow within the sample volume gate is determined based on the Doppler velocity estimates.

20 Claims, 8 Drawing Sheets

US 9,380,992 B2

METHOD AND APPARATUS FOR MEASURING FLOW IN MULTI-DIMENSIONAL ULTRASOUND

BACKGROUND OF THE INVENTION

This invention relates generally to ultrasound imaging, and more particularly, to measuring flow within ultrasound data.

Conventional ultrasound systems are often used to evaluate blood flow, tissue motion and/or strain rate using standard Doppler techniques to measure blood or tissue velocities. These techniques, however, are limited because only the Doppler velocity component oriented along the line of sight can be measured. In many two dimensional imaging cases, such as colorflow and tissue velocity imaging, the line of sight limitation is ignored, primarily due to different positions in the two dimensional space having different Doppler angles. Thus in these cases, only relative velocity rates and direction of motion are generally used and more quantitative information is obtained using pulsed Doppler. In pulsed Doppler, a sample volume may define a unique point in space and the user may specify a flow direction or angle to compensate for the Doppler angle effect. Even then, flow velocity components in the elevational plane, or normal to the imaging (azimuthal) plane, are ignored.

A process called triangulation has been used to eliminate the fundamental line of sight limitation. A sample volume is interrogated in the imaging plane using two different angles, thus providing a mechanism for calculating the two dimensional velocity components to better quantify the flow velocity. The data may be acquired by sequentially transmitting and receiving using two separate steering angles, thus decreasing the overall frame rate, or by separating the transducer elements of the ultrasound probe into separate apertures that transmit and receive at two separate angles simultaneously. While this method accounts for flow velocities measured in the imaging plane, there is no accounting for the third velocity component in the elevational plane.

Therefore, analysis of flow within a volume is limited because flow velocity components that are outside the current imaging plane are not determined.

BRIEF DESCRIPTION OF THE INVENTION

In one embodiment, a method for estimating velocity of flow within an ultrasound dataset comprises defining a sample volume gate on a two-dimensional (2D) image. The 2D image is based on an ultrasonic dataset. Spectral Doppler velocity estimates of flow are detected within the sample volume gate in first and second dimensions that are orthogonal with respect to each other. A true velocity estimate of the flow within the sample volume gate is determined based on the spectral Doppler velocity estimates.

In another embodiment, an ultrasound system comprises a 2D probe having transducer elements positioned in two dimensions. The probe acquires an ultrasonic dataset. A display displays a 2D image based on the ultrasonic dataset. A user input defines a sample volume gate on the 2D image, and the sample volume gate defines a portion of the ultrasonic dataset. A processor performs Doppler velocity calculations on the ultrasonic data within the sample volume gate in first and second dimensions that are orthogonal with respect to each other.

In yet another embodiment, a method for calculating flow dynamics within an ultrasound image comprises defining a sample volume gate within an ultrasound dataset. The sample volume gate comprises first, second and third spatial dimensions. Velocity components are calculated in first and second dimensions based on ultrasound data within the sample volume gate. The first and second dimensions are orthogonal with respect to each other, and the velocity components are acquired based on triangulation techniques. Flow dynamics are calculated over time within the sample volume gate based on the velocity components.

DETAILED DESCRIPTION OF THE INVENTION

Figure 1:
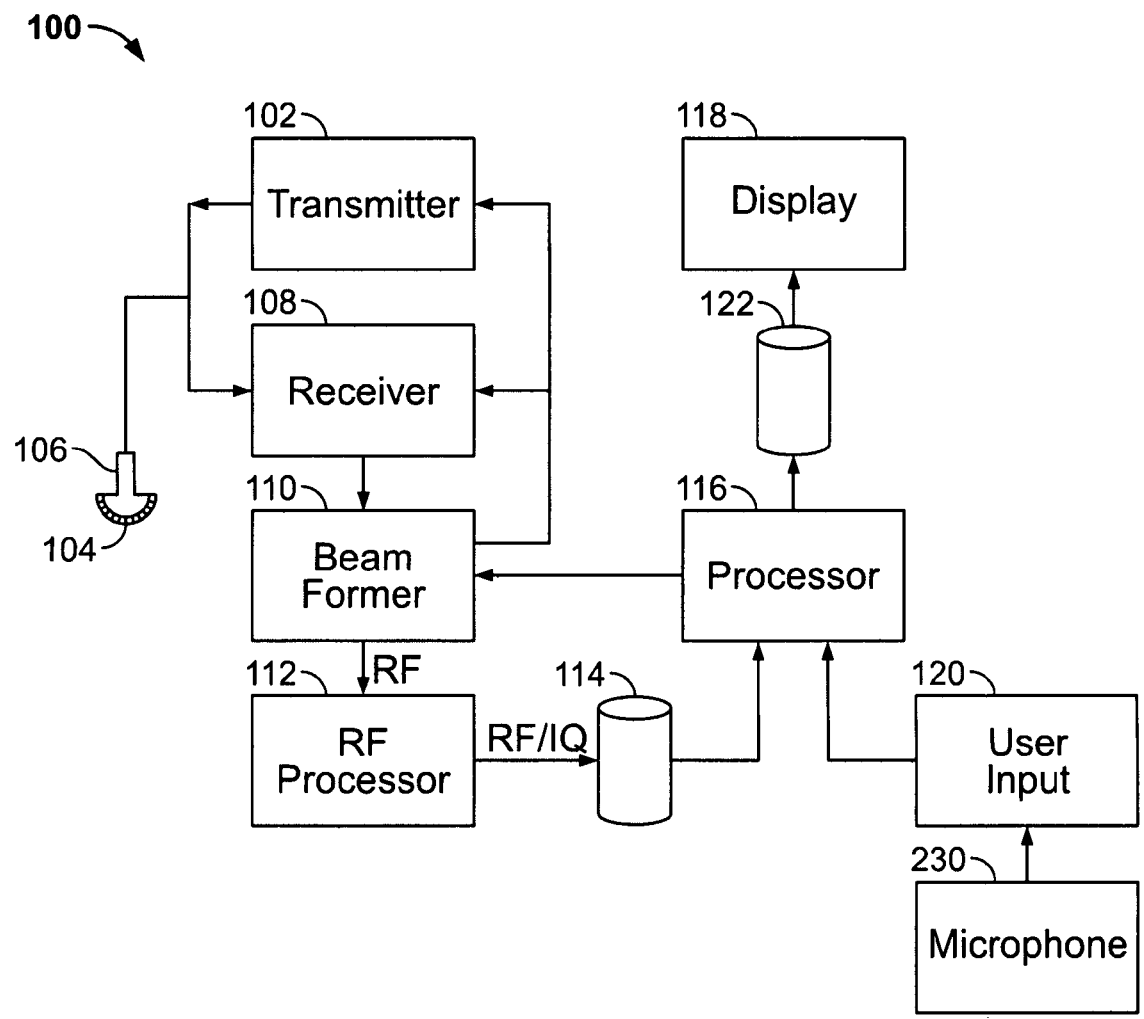
FIG. 1 is a block diagram of an ultrasound system.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

FIG. 1 illustrates a block diagram of an ultrasound system 100. The ultrasound system 100 includes a transmitter 102 that drives transducer elements 104 within a probe 106 to emit pulsed ultrasonic signals into a body. A variety of probe geometries may be used. The ultrasonic signals are backscattered from structures in the body, like blood cells or muscular tissue, to produce echoes that return to the transducer elements 104. The returning echoes are converted back to electrical energy by the transducer elements 104 which are received by a receiver 108. The received signals are passed through a beamformer 110 that performs beamforming (combining the transducer element signals to perform steering and focusing of the beam) and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to an RF/IQ buffer 114 for temporary storage. A user input device 120 as described in more detail below may be used to control operation of the ultrasound system 100, including, to control the input of patient data, scan parameters, identification of a portion of an image to determine flow there-within, a change of scan mode, and the like. This may include using voice commands provided via a microphone 230.

The ultrasound system 100 also includes a processor 116 to process the acquired ultrasound information (i.e., RF signal data or IQ data pairs) and prepare frames of ultrasound information for display on display 118. The processor 116 is adapted to perform one or more processing operations according to a plurality of selectable ultrasound modalities on the acquired ultrasound information. Acquired ultrasound information may be processed in real-time during a scanning session as the echo signals are received.

The ultrasound system 100 may continuously acquire ultrasound information at a frame rate that exceeds fifty frames per second, which is the approximate perception rate of the human eye. The acquired ultrasound information is displayed on the display 118 at a slower frame-rate. A memory 122 is included for storing processed frames of acquired ultrasound information that are not scheduled to be displayed immediately. In an exemplary embodiment, the memory 122 is of sufficient capacity to store at least several seconds worth of frames of ultrasound information. The frames of ultrasound information are stored in a manner to facilitate retrieval thereof according to its order or time of acquisition. The memory 122 may comprise any known data storage medium.

Referring now to the user input 120, various embodiments may be implemented for controlling the ultrasound system 100. Such various embodiments may include control functionality, such as a set of user controls for controlling the ultrasound system 100. The set of user controls may be provided, for example, as part of a touch screen or panel, and as manual inputs, such as user operable switches, buttons, and the like. The set of user controls may be manually operable or voice operated.

Figure 2:
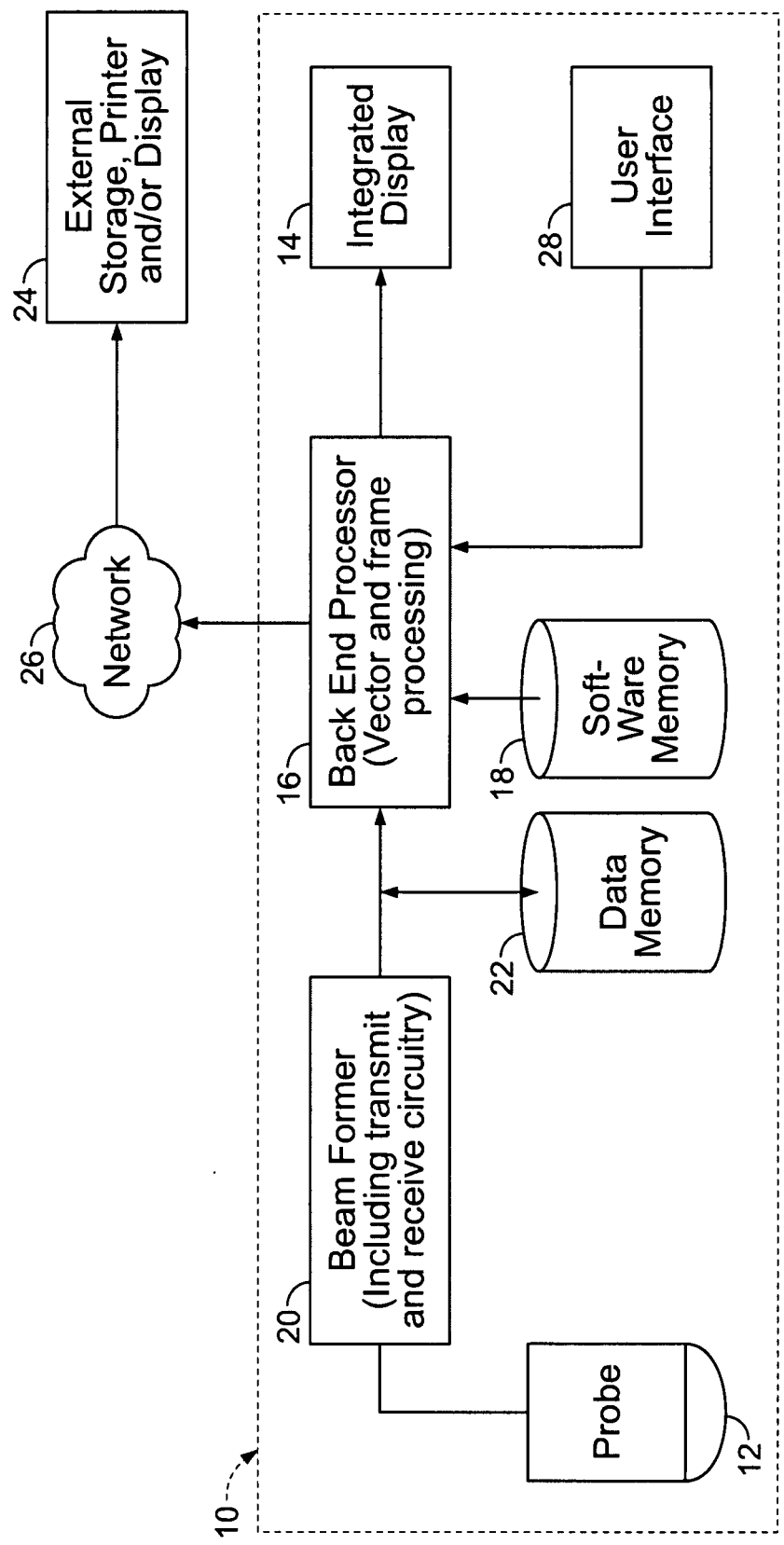
FIG. 2 is a block diagram of a handheld or hand carried ultrasound imaging device having a probe configured to acquire ultrasonic data.

FIG. 2 is a block diagram of a handheld or hand carried ultrasound imaging device 10 having a probe 12 configured to acquire ultrasonic data. Therefore, the hand carried ultrasound imaging device 10 is easily portable by the user. An integrated display 14 (e.g., an internal display) is also provided and is configured to display a medical image. A data memory 22 stores acquired image data, which may be processed by a beamformer 20 in some embodiments of the present invention.

To display a medical image using the probe 12, a back end processor 16 is provided with a software or firmware memory 18 containing instructions to perform frame processing, scan conversion, and resolution selection using acquired ultrasonic image data from the probe 12, possibly further processed by the beamformer 20 in some configurations. Dedicated hardware may be used instead of software for performing scan conversion, or a combination of dedicated hardware and software, or software in combination with a general purpose processor or a digital signal processor.

Software or firmware memory 18 may comprise a read only memory (ROM), random access memory (RAM), a miniature hard drive, a flash memory card, or any kind of device (or devices) configured to read instructions from a machine-readable medium or media. The instructions contained in software or firmware memory 18 further include instructions to produce a medical image of suitable resolution for display on integrated display 14, and to send image data stored in a data memory 22 to an external device 24 in a higher resolution, for example, a resolution higher than the highest resolution that can be displayed on integrated display 14. The image data of higher resolution and/or the ultrasonic data itself may be sent from back end processor 16 to external device 24 via a wired or wireless network (or direct connection, for example, via a serial or parallel cable or USB port) 26 under control of processor 16 and user interface 28. In some embodiments, external device 24 may be a computer or a workstation having a display. Alternatively, external device 24 may be a separate external display or a printer capable of receiving image data from the hand carried ultrasound imaging device 10 and of displaying or printing images that may have greater resolution than the integrated display 14.

A user interface 28 (that may also include integrated display 14) is provided to receive commands from a user and to instruct back end processor 16 to display the acquired image data on integrated display 14, adjust scan parameters, send the acquired image data to the external device 24 in a higher resolution than that displayable on integrated display 14, or both, in accordance with the commands from the user.

Figure 3:
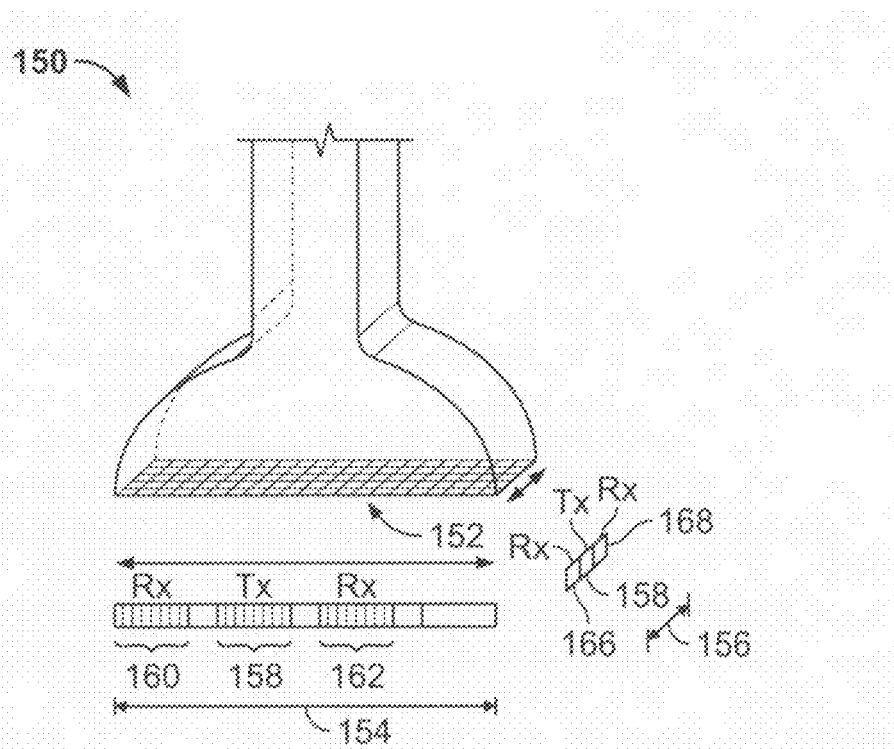
FIG. 3 illustrates a two-dimensional (2D) probe formed in accordance with an embodiment of the present invention that may be used to acquire ultrasonic data over time.

FIG. 3 illustrates a two-dimensional (2D) probe 150 that may be used to acquire ultrasonic data having up to three spatial components (X, Y and Z) and one time component. The probe 150 may be used with either of the system 100 of FIG. 1 or the hand carried ultrasound imaging device 10 of FIG. 2. The probe 150 has a plurality of transducer elements 152 arranged along first and second dimensions 154 and 156.

Figure 4:
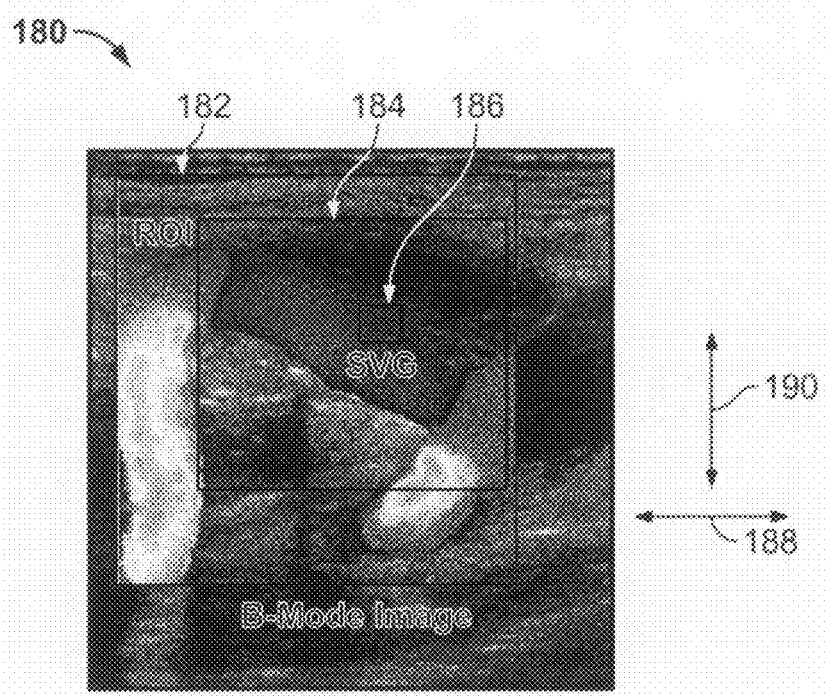
FIG. 4 illustrates a B-mode image acquired by the 2D probe of FIG. 3 with a sample volume gate indicated thereon in accordance with an embodiment of the present invention.

FIG. 4 illustrates a B-mode image 180 acquired by the 2D probe 150 of FIG. 3 that may be displayed on the displays 118 and 14 of FIGS. 1 and 2, respectively. The B-mode image 180 may be the imaging or azimuthal plane and has first and second dimensions 188 and 190. The B-mode image 180 represents the slice of data acquired by transducer elements 152 located in the elevational center of the probe 150 (the elevational direction corresponding to the second dimension 156 of FIG. 3). For example, if the probe acquires 64 slices in the elevation dimension, the B-mode image 180 is representative of slice 32.

A color flow box 182 may be selected using the user input 120 (FIG. 1) or may be selected automatically by the processor 116. Flow dynamics on the B-mode image 180 may be displayed in color within the color flow box 182. Optionally, no color flow box 182 may be defined. A region of interest (ROI) 184 is defined and may be positioned by the user within the color flow box 182, such as by using the user input 120 and user interface 28. In this example, the ROI 184 may not be positioned outside of the color flow box 182 and the field of view or size of the probe 150 may determine the relative size of the ROI 184.

A sample volume gate 186 may be placed and moved within the ROI 184 to a desired region where the user wishes to evaluate flow. In some situations, depending upon the scanning geometry used during triangulation estimations, the ROI 184 and/or the sample volume gate 186 may be placed at the extreme edges of the B-mode image 180. The user may also change a size and a shape of the sample volume gate 186 along the first and second dimensions 188 and 190 within the displayed B-mode image 180. The sample volume gate 186 is illustrated on the B-mode image 180 as a square, however, the sample volume gate 186 defines a three-dimensional (3D) area in space, such as a cube or 3D rectangle. By way of example, the sample volume gate 186 may be small, such as one pixel cubed.

Triangulation is performed on ultrasound data within the sample volume gate 186 to achieve a 2D Doppler spectrum and for other flow calculations. Flow parameters may include, but are not limited to, peak velocity, flow direction, spectral content of the flow, and the like. While the system 100 collects 2D data throughout the field of view of the probe 150, at least a portion of a three-dimensional (3D) dataset may be acquired within the sample volume gate 186.

Returning to FIG. 3, to accomplish triangulation in the first dimension 154, the transducer elements 152 may be divided into a transmit aperture 158 and first and second receive apertures 160 and 162. In the second dimension 156, the transducer elements 152 of the probe 150 may be divided into the transmit aperture 158 and first and second receive apertures 166 and 168. In this embodiment, as the B-mode image 180 corresponds to the center of the elevational field of view of the probe 150, the sample volume gate 186 is also positioned at the elevational center.

The triangulation in the azimuthal and elevational planes may be based at least in part on the size of the aperture of the probe 150. In each plane, the receive apertures may be the same size and placed symmetrically on either side of the transmit aperture. Alternatively, the first and second receive apertures 160 and 162 may be asymmetrically placed with respect to the transmit aperture and/or may be different in size with respect to each other. It should be understood that not all of the transducer elements 152 may be used and that the transmit and receive apertures may be separate from each other and/or overlapped with respect to each other. For example, one of the first and second receive apertures 160 and 162 may use some or all of the same transducer elements 152 as the transmit aperture 158.

The size and positioning of each aperture within the 2D array of the transducer elements 152 may also be based on the position of the sample volume gate 186 with respect to the field of view of the probe 150 and may be determined and/or adjusted by the processor 116 to maximize the 4D flow accuracy. For example, flow accuracy may be maximized by balancing the size and position of the receive apertures with respect to the transmit aperture and the sample volume gate. In general, the larger and further apart the receive apertures are with respect to each other, the better the triangulation (or velocity) estimate will be. The directionality of the individual transducer elements 152 is also considered, however, and thus the receive apertures are not positioned a distance apart that exceeds the directional capability of the transducer elements 152. It should be understood that other triangulation techniques may be used.

Flow velocity components or Doppler velocity estimates are then acquired within the imaging or azimuthal plane (the plane of the B-mode image 180) and within the elevational plane, which is orthogonal to the azimuthal plane. Depending upon the capabilities of the system 100, the velocity estimates may be acquired sequentially or simultaneously within the two planes.

Figure 5:
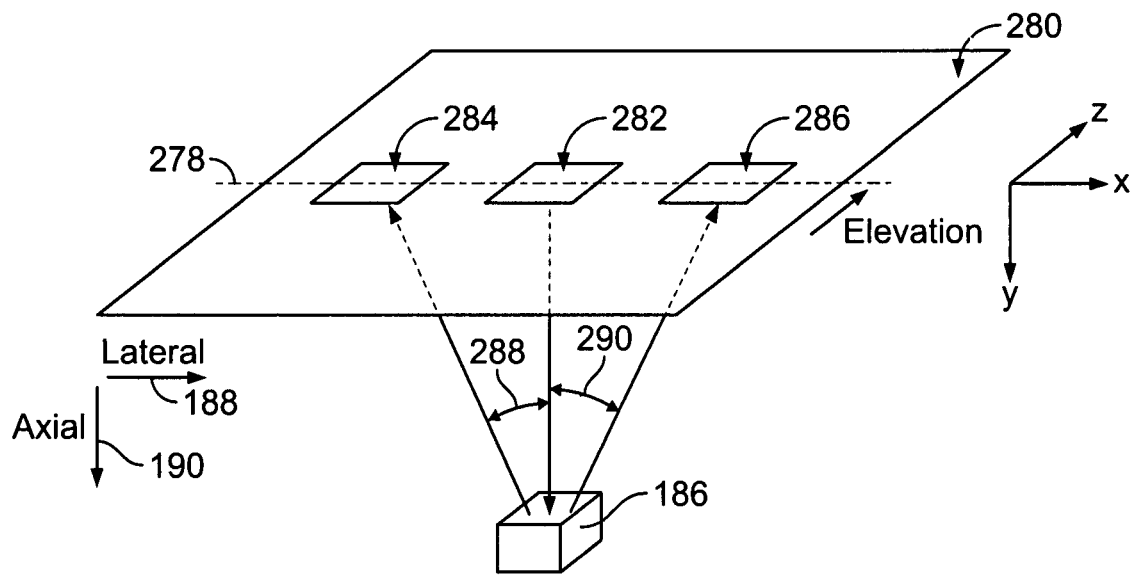
FIG. 5 illustrates an example of using triangulation to acquire Doppler velocity estimates in the azimuthal dimension in accordance with an embodiment of the present invention.
Figure 6:
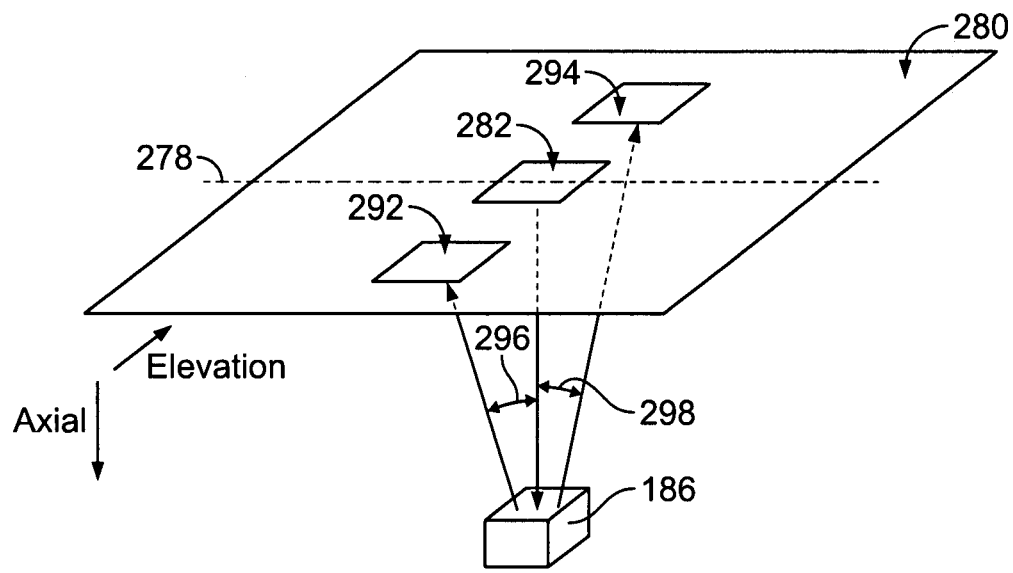
FIG. 6 illustrates an example of using triangulation to acquire Doppler velocity estimates in the elevational dimension in accordance with an embodiment of the present invention.

FIGS. 5 and 6 illustrate examples of using triangulation to acquire Doppler velocity estimates in the azimuthal and elevational dimensions, respectively, of the B-mode image 180 of FIG. 4. A 2D array 280 of transducer elements is illustrated having elevational center 278. A user has defined the sample volume gate 186 in space by moving the sample volume gate 186 in the first and second dimensions 188 and 190 of the B-mode image 180 and/or by changing the size and shape of the sample volume gate 186. In this example, the B-mode image 180 is acquired at the elevational center 278 of the field of view of the probe 150.

Once the sample volume gate 186 is positioned, the processor 116 calculates optimal positions of receive and transmit apertures, which may be based on tables derived from simulations. For example, triangulation techniques are typically most accurate when processing data within the center of the field of view of the probe 150 (FIG. 3). In general, the presence of the ROI 184 limits the movement in space of the sample volume gate 186 with respect to the FOV of the probe 150, as seen in FIG. 4. Depending upon the geometry of the transmit and receive apertures, placement of ROI and/or sample volume gate on the reference image(s) may be limited, at least in part, to central regions of the field of view of the probe 150. However, it should be understood that the placement of either the ROI or the sample volume gate is not limited to the center of the field of view of the probe 150.

Turning to the azimuthal dimension of FIG. 5, the processor 116 defines transmit aperture 282 and first and second receive apertures 284 and 286. The first and second receive apertures 284 and 286 may be positioned equidistant on either side of the transmit aperture 282. Alternatively, the positioning may be asymmetric. In the elevational dimension of FIG. 6, as the B-mode image 180 is the center of the elevational field of view of the probe 150, in this embodiment the processor 116 assumes that the center of the elevational plane is to be processed. The processor 116 may use the transmit aperture 282 as previously defined, and defines third and fourth receive apertures 292 and 294.

The processor 116 modifies the transmit and receive beamforming to steer and focus the transmit and receive apertures only onto the sample volume gate. The beamformer 110 transmits ultrasound beams from the transmit aperture 282 and receives ultrasound beams with the first and second apertures 284 and 286, which detect beams at first and second angles 288 and 290. The first and second angles 288 and 290 may be the same angular distance from the transmit beam, or may be different. The processor 116 then calculates spectral Doppler estimates in the axial direction and spectral Doppler estimates in the lateral direction based at least on the first and second angles 288 and 290. Therefore, the processor 116 simultaneously detects spectral Doppler estimates in two different directions based on ultrasound information within the sample volume gate 186.

The beamformer 110 transmits ultrasound beams from the transmit aperture 282 and receives ultrasound beams with the third and fourth apertures 292 and 294 at third and fourth angles 296 and 298, respectively, from the transmit beam. The processor 116 may then calculate spectral Doppler estimates in the axial and elevational dimensions based at least on the third and fourth angles 296 and 298. Three dimensional flow components (e.g. peak velocity, mean velocity, peak flow, etc) may be extracted from the spectral Doppler estimates.

The axial components calculated in the azimuthal and elevational dimensions should be the same value. The processor 116 may combine the spectral Doppler estimates from the three dimensions to calculate a true velocity magnitude and a true velocity direction within the sample volume gate 186. For example, the processor 116 uses the flow information (or Doppler shift information) detected in the elevational plane to provide the flow direction component needed to process the flow data acquired in the azimuthal plane. Therefore, the processor 116 may calculate a true 3D spectral estimate or velocity estimate without further input from the user. It should be understood that a single velocity estimate may also be determined, such as by derivation from the spectral estimates. As the processor 116 continues to repeatedly acquire the triangulation information in both planes over time, a spectrum of values is acquired, such as 4D velocity data, and 3D velocity estimates over time may be calculated.

Figure 7:
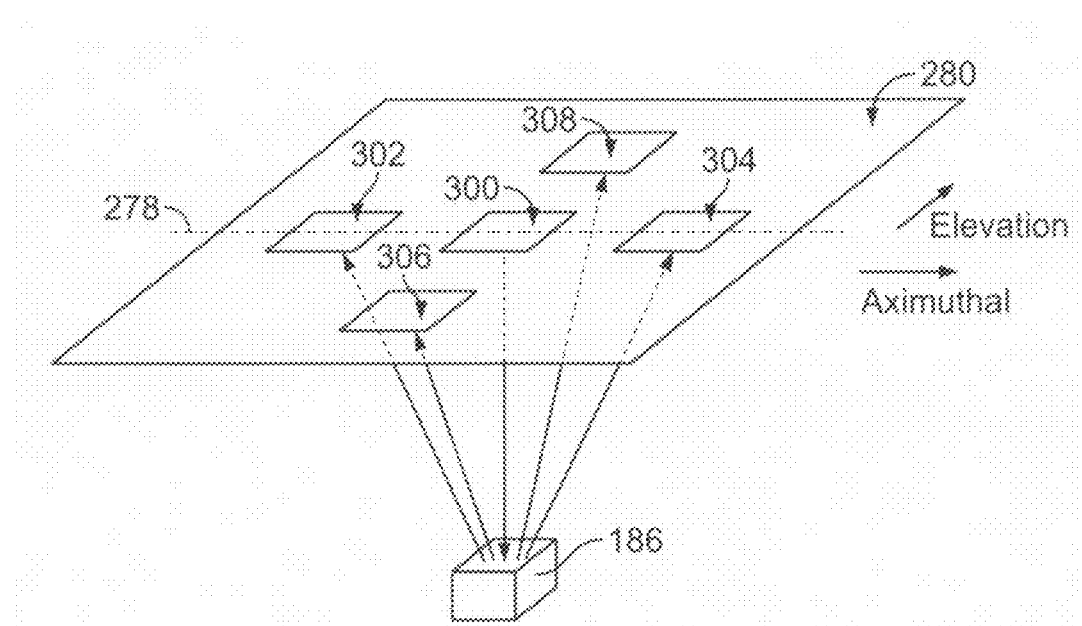
FIG. 7 illustrates an example of using triangulation to simultaneously acquire Doppler velocity estimates in both the azimuthal and elevational dimensions in accordance with an embodiment of the present invention.

FIG. 7 illustrates an example of using triangulation to simultaneously acquire Doppler velocity estimates in both the azimuthal and elevational dimensions. A single transmit aperture 300 is defined with first and second receive apertures 302 and 304 in the azimuthal dimension and third and fourth receive apertures 306 and 308 in the elevational dimension. The beamformer 110 transmits to the sample volume gate 186 with the transmit aperture 300, and the first, second, third and fourth receive apertures 304-308 simultaneously detect received signals.

Figure 8:
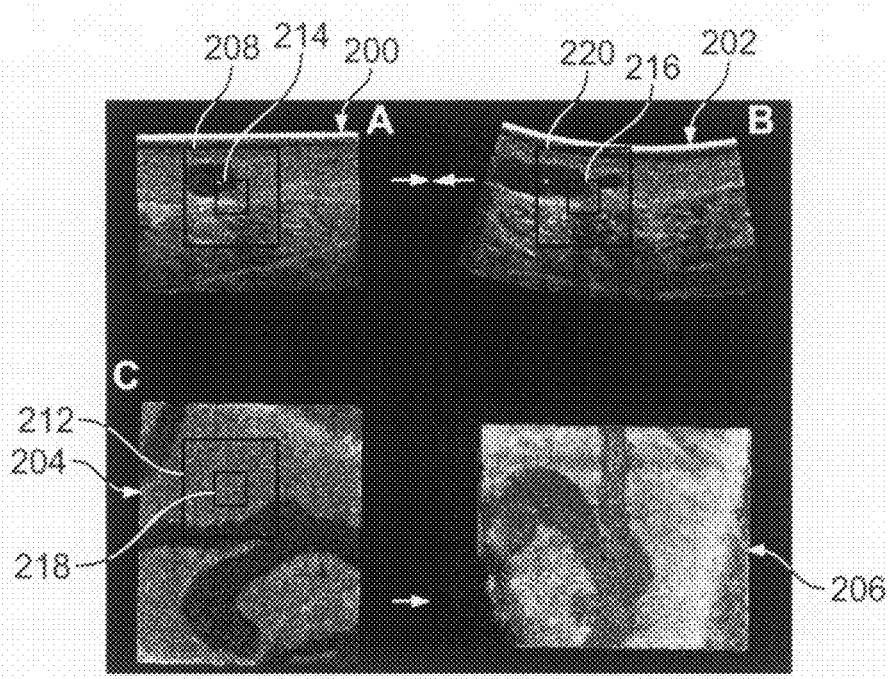
FIG. 8 illustrates multiple planes that may be used to position the sample volume gate in accordance with an embodiment of the present invention.

The user may wish to visualize and adjust the sample volume gate within elevational planes other than the B-mode image 180 centered at the elevational center of the probe. FIG. 8 illustrates multiple planes that may be used to position the sample volume gate. The multiple planes may be three orthogonal planes, such as A plane 200, B plane 202, and C plane 204, and may be displayed together with a volume rendered image 206. In this example, the A plane 200 may be the azimuthal plane, such as the B-mode image 180 of FIG. 4. It should be understood that the displayed planes are not limited to planes that are orthogonal with respect to each other, and that two planes may be used. For example, the user may display other planes or images to better view the anatomy through which the flow is to be determined.

The processor 116 places A, B, and C ROIs 208, 210 and 212 on the A, B and C planes 200, 202 and 204, respectively. In this example, color flow is not in use, and thus no color flow boxes are indicated. The size and position of the A, B and C ROIs 208, 210 and 212 are based at least in part on the geometry of the imaging situation, as discussed previously. Based on the position of the ROI, the processor 116 may determine triangulation strategies and aperture management using strategies known in the art to achieve the best possible estimate. Optionally, the user may wish to adjust the position of the probe 180 and/or scanning parameters to position an area of interest near the center of the FOV of the probe 150.

A, B and C sample volume gates 214, 216 and 218 are indicated within the A, B and C ROIs 208, 210 and 212, respectively. Although the A, B and C sample volume gates 214, 216 and 218 are indicated with different item numbers, it should be understood that their position in 3D space is the same. The user may manipulate the size and position of each of the A, B and C sample volume gates 214, 216 and 218 individually while viewing the corresponding image plane, and thus is able to manipulate the sample volume gate within the 3D imaging space. Adjusting a sample volume gate in one plane may change how one or more of the sample volume gates is displayed in the other two planes.

Figure 9:
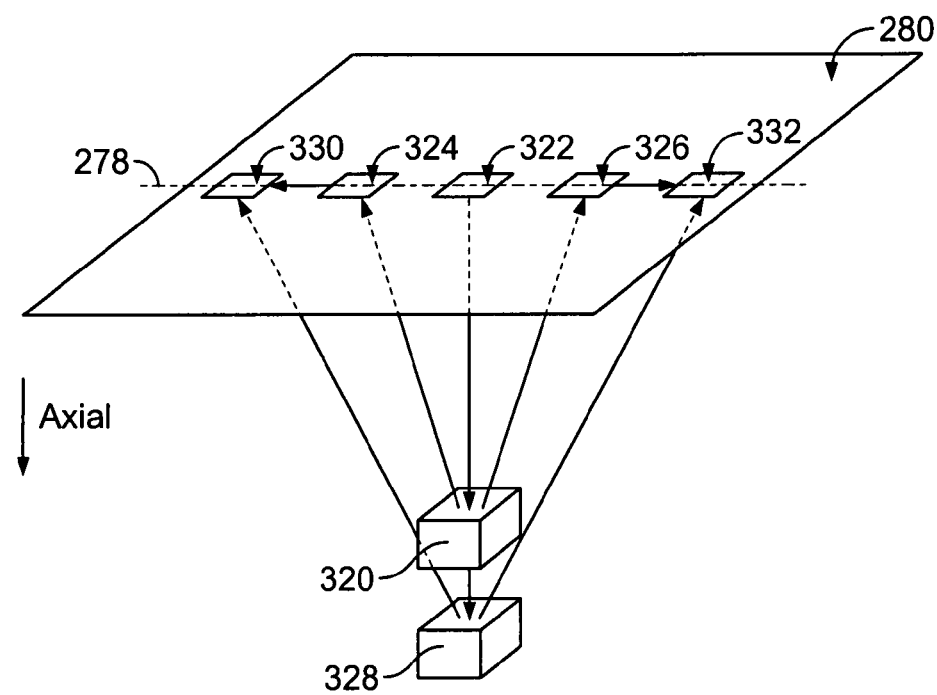
FIG. 9 illustrates an example of positioning transmit and receive apertures in accordance with an embodiment of the present invention when the sample volume gate is moved in the axial direction.
Figure 10:
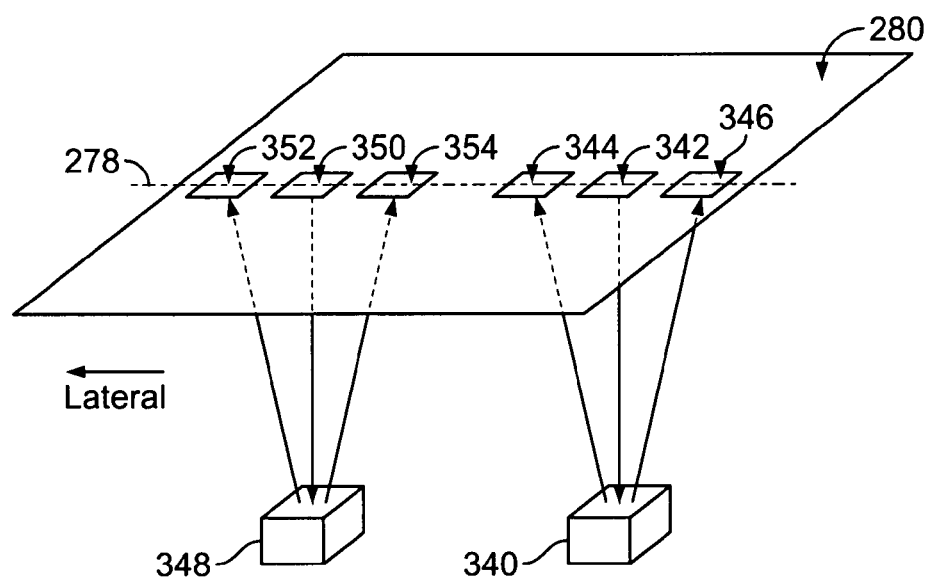
FIG. 10 illustrates an example of positioning transmit and receive apertures in accordance with an embodiment of the present invention when the sample volume gate is moved in the lateral direction.

FIGS. 9 and 10 illustrate examples of positioning the transmit and receive apertures based on movement of the sample volume gate in the axial and lateral directions, respectively. FIGS. 9 and 10 will be discussed with reference to the azimuthal plane, such as the A plane 200 of FIG. 8. In FIG. 9, when the sample volume gate 214 is at first position 320, first and second receive apertures are located at first and second receive positions 324 and 326, respectively, on either side of transmit aperture 322. When the user moves the sample volume gate 214 in the axial direction to second position 328, such as to position the sample volume gate further from the surface of the probe 150, the transmit aperture 322 remains in the same position and the first and second receive apertures are positioned further from the transmit aperture 322 at third and fourth receive positions 330 and 332, respectively. Although not shown, moving the sample volume gate in the axial direction may have a similar effect on the positioning of the transmit and receive apertures in the elevational dimension.

Turning to FIG. 10, when the sample volume gate 214 is at first position 340, the transmit aperture may be at first transmit position 342 and first and second receive apertures are positioned in first and second receive positions 344 and 346, respectively, on either side of the first transmit position 342. After the user moves the sample volume gate 214 laterally to second position 348, the transmit aperture is moved to second transmit position 350 and the first and second receive apertures are positioned at third and fourth transmit positions 352 and 354, respectively. Therefore, all three apertures may be shifted laterally. The size of the apertures may change based on the desired receive angles, as well as the distance of the transmit aperture from the edge of the probe 150.

Figure 11:
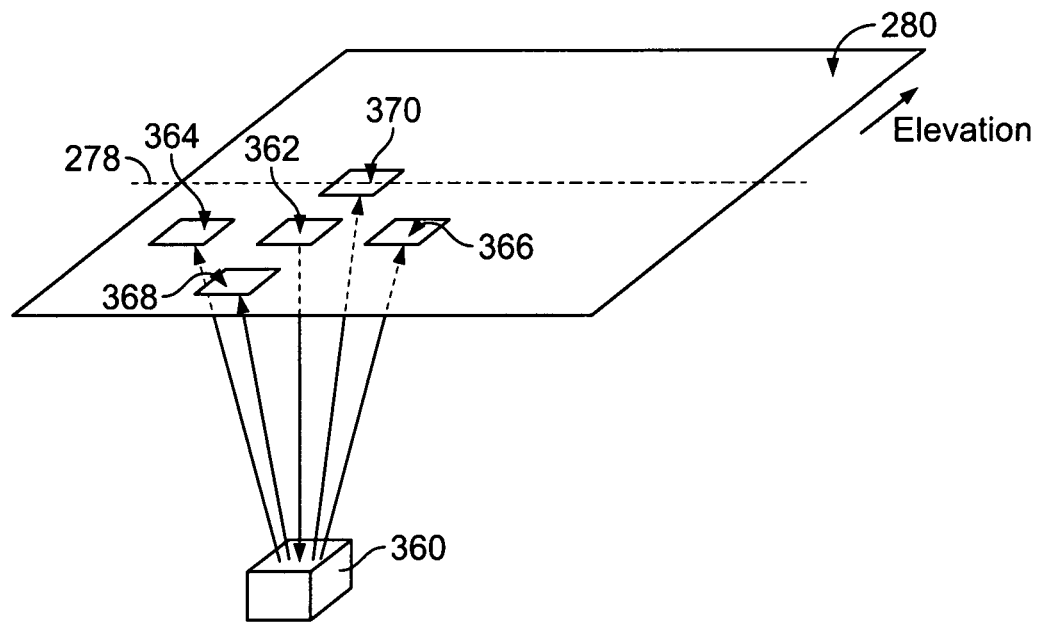
FIG. 11 illustrates an example of positioning transmit and receive apertures in accordance with an embodiment of the present invention when the sample volume gate is moved in the elevational direction.

Both of the examples as illustrated in FIGS. 9 and 10 move the sample volume gate within the center elevational plane of the probe 150. FIG. 11 illustrates the positioning of transmit and receive apertures when the sample volume gate is moved within the elevational plane, such as within the C plane 204 of FIG. 8. The sample volume gate has been moved to position 360 that is located away from the elevational center 278 of the 2D array 280. The transmit and receive apertures are positioned with respect to the position 360 of the sample volume gate 218. In this example, transmit aperture 362 is used in both the azimuthal and elevational directions. First and second receive apertures are positioned at first and second receive positions 364 and 366 in the azimuthal dimension and third and fourth receive apertures are positioned in third and fourth receive positions 368 and 370 in the elevational dimension. Separate hardware and/or software may be provided within the beamformer 110, transmitter 102 and receiver 108 circuitries to allow the simultaneous collection of velocity estimates in both the azimuthal and elevational dimensions.

Figure 12:
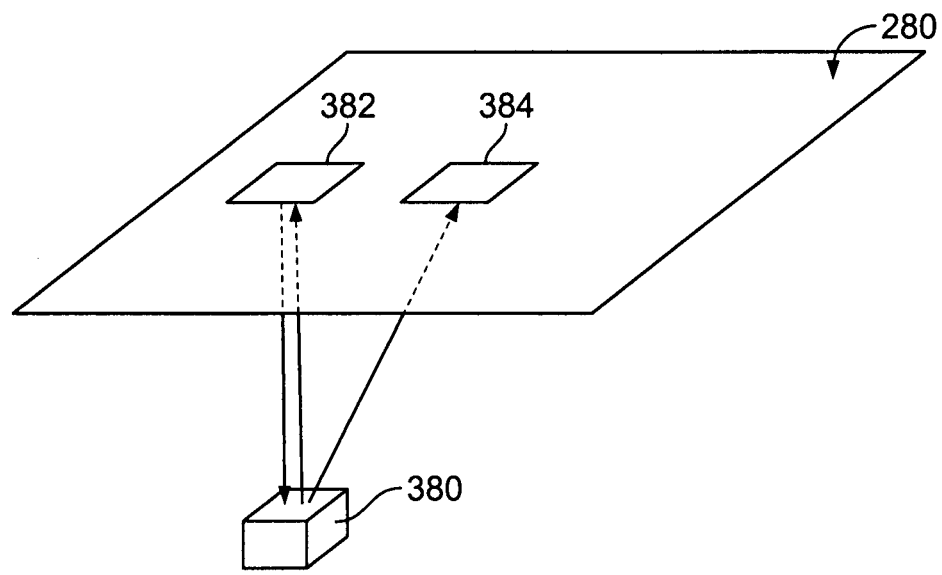
FIG. 12 illustrates an example wherein overlap exists between the transmit aperture and one of the receive apertures in the azimuthal dimension in accordance with an embodiment of the present invention.

FIG. 12 illustrates an example wherein overlap exists between the transmit aperture and one of the receive apertures, such as when the sample volume gate is positioned near an edge of the probe field of view. The azimuthal dimension will be discussed, however, the following geometric positioning information relates equally to the elevational dimension. The user may position the sample volume gate at position 380, located at a far edge of the field of view of the probe 150, such as along an edge of the A plane 200 of FIG. 8. In this example, transducer elements may not be available to form separate receive apertures on both sides of the transmit aperture in the azimuthal dimension. Therefore, transducer element(s) located at transmit/receive position 382 are used for both transmit and receive functions. The beamformer may transmit to the position 380 of the sample volume gate from the transmit/receive position 382. The transducer elements at the transmit/receive position 382 then receive signals at the same time as second receive position 384 to compute the Doppler estimates in the azimuthal dimension. Although the transmit/receive position 382 is illustrated as using the same transducer elements, a transmit and receive position may be defined which uses a partial overlap of transducer elements.

Figure 13:
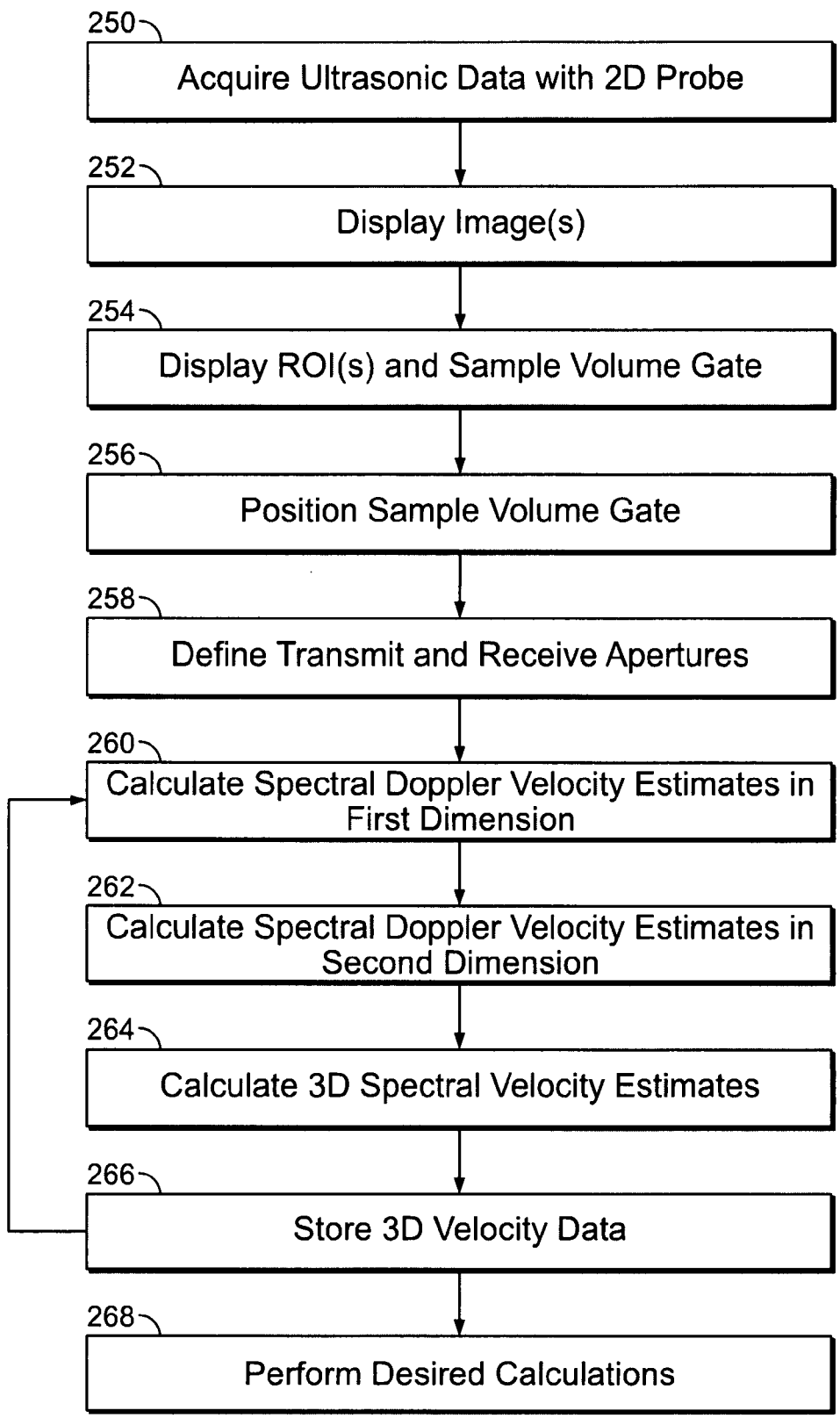
FIG. 13 illustrates a method for acquiring 4D velocity data in accordance with an embodiment of the present invention.

FIG. 13 illustrates a method for determining 4D velocity data associated with blood or tissue within an ultrasonic dataset. At 250, the user acquires ultrasonic data with the probe 150 (shown in FIG. 3) that has two dimensions of transducer elements 152. At 252, the user may select and display at least one image from within the ultrasonic data. For example, the B-mode image 180 (FIG. 4) may be displayed. Alternatively, three orthogonal views, such as the A, B and C planes 200, 202 and 204 of FIG. 8, or a plurality of other views may be displayed. The user may also initiate a scanning protocol that automatically displays one or more predetermined images, as well as initiates the automatic display of information below, such as by selecting and positioning the ROI(s) and the sample volume gate.

At 254, the processor 116 may display at least one ROI on the displayed image(s), the size and position of which may be based at least on the geometry of the probe 150. The processor 116 also displays a sample volume gate within each ROI. At 256, the user may position the sample volume gate within the ROI(s) on the images that are displayed, as well as change the size and/or shape of the displayed sample volume gate. The sample volume gate indicates the area within the ultrasonic data from which the 3D and 4D flow data is to be derived. Alternatively, the user may position the sample volume gate without the use of an ROI, such as to achieve a position of the sample volume gate at the edge of the field of view of the probe 150.

At 258, the processor 116 determines the positions, size and receive angles of the transmit and receive apertures in orthogonal planes, such as in the azimuthal and elevational dimensions. The processor 116 bases the positions of the transmit and receive apertures on the position of the sample volume gate with respect to the probe field of view, as well as data used to define and/or limit receive angles. As discussed previously, the transmit and receive apertures may be geometrically different from one another, or the transmit and receive apertures in at least one direction, such as discussed in FIG. 12, may overlap fully or partially.

At 260, the beamformer 110 transmits and receives using transmit and receive apertures defined in the first dimension. The processor 116 calculates spectral Doppler velocity estimates within the first dimension using triangulation. Alternatively, other methods may be used to calculate the velocity. The first dimension may be the azimuthal or current imaging plane, or a different user designated or predetermined plane. If the first dimension is the azimuthal plane, the Doppler velocity estimates may be in the axial and lateral directions. At 262, the processor 116 calculates spectral Doppler velocity estimates within a second dimension, such as by using triangulation. The second dimension may intersect, bisect or otherwise cross the first plane within the area of the sample volume gate. The second dimension may be the elevational plane, which is orthogonal to the azimuthal plane, such that the direction of flow across the azimuthal plane may be identified. In this case, the spectral Doppler velocity estimates may be in the axial and elevational directions. Alternatively, the spectral Doppler velocity estimates in both dimensions may be acquired simultaneously.

At 264, the processor 116 calculates 3D spectral velocity estimates based on the spectral Doppler velocity estimates determined at 260 and 262. The 3D spectral velocity estimates takes into account flow velocity components that are outside of the azimuthal imaging plane (the B-mode image 180 of FIG. 4) to provide a value of true 3D flow within the sample volume gate.

At 266, the processor 116 may store the 3D velocity estimates in the memory 122, and at 268, the processor 116 may perform desired calculations based on the 3D velocity estimates of 264. For example, some measurements as discussed below may be based on instantaneous sampling, while other measurements are based on multiple points over time. The method returns to 260 from 266 to continue to acquire and calculate velocity data over time, or 4D velocity data. As more velocity estimates are acquired, at 268 the processor 116 may accomplish measurements that require multiple time points, such as analyzing flow dynamics.

The 4D (3D over time) flow technique described herein may be used to perform measurements and calculations typically used in standard 2D pulsed Doppler. For example, a Doppler trace associated with the ultrasound data may be displayed on the display 118 of FIG. 8. Measurements that are based on instantaneous sampling of the Doppler spectrum, such as peak flow may be performed in either real time or using a frozen Doppler trace. Measurements that require multiple time points in the Doppler spectrum may be performed on a frozen Doppler trace. These measurements may include, but are not limited to, pulsatility index, resistive index, peak systole/end diastole (PS/ED) or ED/PS ratios, measurement of the relative heights of systolic peaks (A/B ratio), maximum pressure gradient, mean pressure gradient, stroke volume, and heart rate. As with conventional pulsed Doppler these measurements may be obtained either through automatic detection of the Doppler trace characteristics or by the user selecting the appropriate points in the cardiac cycle.

The speed and direction of flow can be displayed along with the 2D B-mode image 180 (FIG. 4) or in the A/B/C plane volume set of FIG. 8. For example, a Doppler spectrum may be displayed or components indicating more than one spatial dimension may be displayed. The data may be displayed in the images, as an overlay, or separately.

In a further embodiment, ultrasound data within the ROI rather than within the smaller sample volume gate may be used for velocity component calculations. The user may reduce the dimensions of the previously defined ROI, such as the ROI 184 of FIG. 4, and move the ROI within the 2D B-mode image 180. Alternatively, the user may reduce the dimensions of the A, B and/or C ROIs 208, 210 and 212, and move the A, B and C ROIs within the volume space of the A, B and C planes 200, 202 and 204, respectively. The processor 116 may then determine the maximum flow at peak systole or end diastole locations and values within the ROI 184 (or A, B and C ROIs 208, 210 and 212) as a function of time in the 4D data set. In yet another embodiment, the A, B and C ROIs 208, 210 and 212 and/or the sample volume gates 214, 216 and 218 may be used to determine values, such as peak flow, within a spatial area.

The aforementioned 4D velocity calculating techniques may also be applied to any imaging technique that determines velocity using the Doppler technique, such as tissue velocity imaging and strain rate imaging. In addition, it should be understood that the 4D velocity calculating techniques may also be accomplished with other triangulation techniques, such as using simultaneous multi-subaperture techniques, and multi-steered frame methods.

A technical effect of at least one embodiment is to achieve Doppler imaging in 3D using triangulation. The user does not need to enter a flow direction and true 3D velocity data may be determined. A sample volume gate is adjusted on one or more displayed images to define a desired area for interrogation. The sample volume gate may be adjusted in three dimensions. Transmit and receive geometries are determined in two dimensions, such as two orthogonal planes, to accommodate different positions and sizes of the sample volume gate.

While the invention has been described in terms of various specific embodiments, those skilled in the art will recognize that the invention can be practiced with modification within the spirit and scope of the claims.

What is claimed is:

1. A method for estimating velocity of flow within an ultrasound dataset, the method comprising:
    defining a sample volume gate on a two-dimensional (2D) image, the 2D image being based on an ultrasonic dataset;
    determining a transmit aperture having one or more transducer elements of an ultrasound probe for transmitting at least one signal, first and second receive apertures that are disposed on opposite sides of the transmit aperture in a first dimension, and third and fourth receive apertures that are disposed on opposite sides of the transmit aperture in a second orthogonal dimension, the first, second, third, and fourth receive apertures being separate from the transmit aperture and each including one or more transducer elements;
    changing one or more of a first position of the transmit aperture, a second position of the first and second receive apertures, or a third position of the third and fourth receive apertures in the probe in response to an operator changing a position of the sample volume gate by altering which of the transducer elements are included in one or more of the transmit aperture, the first receive aperture, the second receive aperture, the third receive aperture, or the fourth receive aperture;
    detecting, with the first, second, third, and fourth receive apertures, spectral Doppler velocity estimates of flow within the sample volume gate based on the at least one signal that is transmitted by the transducer elements in the transmit aperture, the spectral Doppler velocity estimates being detected in the first and second dimensions; and
    determining a true velocity estimate of the flow within the sample volume gate based on the spectral Doppler velocity estimates.

2. The method of claim 1, wherein the first and second dimensions are azimuthal and elevational dimensions, respectively, the detecting further comprising performing first and second triangulation calculations in the azimuthal and elevational dimensions, respectively.

3. The method of claim 1, wherein the transmit aperture is a single transmit aperture comprising one or more of the transducer elements disposed side-by-side.

4. The method of claim 1, further comprising:
    determining the transmit aperture in the first dimension with respect to the sample volume gate; and
    determining the first and second receive apertures in the first dimension with respect to at least the transmit aperture and the position of the sample volume gate, the transmit aperture and the first and second receive apertures being used to detect the spectral Doppler velocity estimates in the first dimension.

5. The method of claim 1, further comprising:
    displaying at least two orthogonal planes based on the ultrasonic dataset, the at least two orthogonal planes corresponding to the first and second dimensions, respectively; and
    displaying the sample volume gate on the at least two orthogonal planes, the sample volume gate being adjustable in three dimensions to move the one or more of the first position of the transmit aperture, the second position of the first receive aperture and the second receive aperture, or the third position of the third receive aperture and the fourth receive aperture in the probe.

6. The method of claim 1, further comprising:
    displaying first, second and third planes based on the ultrasonic dataset, the first, second and third planes being orthogonal with respect to each other;
    displaying the sample volume gate on the first, second and third planes; and
    adjusting the sample volume gate on the first plane, the sample volume gate displayed on the second and third planes being automatically adjusted based on the adjusting on the first plane, wherein the one or more of the first position of the transmit aperture, the second position of the first receive aperture and the second receive aperture, or the third position of the third receive aperture and the fourth receive aperture in the probe is moved based on the adjusting of the sample volume gate.

7. The method of claim 1, wherein changing one or more of the first position the transmit aperture, the second position of the first receive aperture and the second receive aperture, or the third position of the third receive aperture and the fourth receive aperture includes altering a distance between the transmit aperture and one or more of the first, second, third, or fourth receive apertures by when the sample volume gate is moved toward or away from the probe.

8. The method of claim 1, wherein changing one or more of the first position of the transmit aperture, the second position of the first receive aperture and the second receive aperture, or the third position of the third receive aperture and the fourth receive aperture includes altering a lateral position of one or more of the transmit aperture, the first receive aperture, the second receive aperture, the third receive aperture, or the fourth receive aperture within the probe when the sample volume gate is laterally moved relative to the probe.

9. The method of claim 1, wherein changing one or more of the first position of the transmit aperture, the second position of the first receive aperture and the second receive aperture, or the third position of the third receive aperture and the fourth of receive aperture includes changing which transducer elements are included in one or more of the transmit aperture, the first receive aperture, the second receive aperture, the third receive aperture, or the fourth receive aperture.

10. The method of claim 9, wherein relative positions of the transmit aperture and the first, second, third, and fourth receive apertures remain unchanged while the transmit aperture and the first, second, third, and fourth receive apertures are laterally moved within the probe.

11. The method of claim 1, wherein determining the transmit aperture and the first, second, third, and fourth receive apertures includes selecting one or more common transducer elements to be included in two or more of the transmit aperture or the first, second, third, and fourth receive apertures.

12. The method of claim 1, further comprising switching the transmit aperture to a transmitting and receiving aperture when one or more of the first, second, third, or fourth receive apertures is moved toward an edge of the probe, the transmitting and receiving aperture configured to transmit one or more signals and detect one or more spectral Doppler velocity estimates of flow.

13. An ultrasound system, comprising:
a two-dimensional (2D) probe having transducer elements positioned in two dimensions, the probe acquiring an ultrasonic dataset;
a display for displaying a 2D image based on the ultrasonic dataset;
a user input for defining a sample volume gate on the 2D image, the sample volume gate defining a portion of the ultrasonic dataset; and
a processor for defining a transmit aperture having at least one of the transducer elements within the probe, a first receive aperture and a second receive aperture disposed on opposite sides of the transmit aperture in a first dimension, and a third receive aperture and a fourth receive aperture disposed on opposite sides of the transmit aperture in a second orthogonal dimension, the first, second, third, and fourth receive apertures each including one or more transducer elements in the probe, the processor further performing Doppler velocity calculations on the ultrasonic data within the sample volume gate in first and second dimensions using ultrasound signals transmitted by the same transmit aperture and Doppler velocity estimates acquired by the first, second, third, and fourth receive apertures, the first and second dimensions being orthogonal with respect to each other,
wherein the processor changes one or more of a first position of the transmit aperture, a second position of the first and second receive apertures, or a third position of the third and fourth receive apertures in the probe when the user input changes a location of the sample volume gate, the one or more of the first position, the second position, or the third position changed by altering which of the transducer elements are included in one or more of the transmit aperture, the first receive aperture, the second receive aperture, the third receive aperture, or the fourth receive aperture.

14. The system of claim 13, wherein the velocity calculations in the second dimension provide a direction of flow with respect to the first dimension.

15. The system of claim 13, wherein the processor adjusts a size of the transmit aperture based on a position of the sample volume gate within the 2D image.

16. The system of claim 13, further comprising:
the display displaying at least a second image based on the ultrasonic dataset, the second image being orthogonal to the 2D image and comprising the portion of the ultrasonic dataset defined by the sample volume gate; and
the user input adjusting the sample volume gate in three dimensions.

17. The system of claim 13, wherein the system is one of a handheld or hand carried ultrasound imaging device.

18. The system of claim 13, wherein the processor alters a distance between the transmit aperture and one or more of the first, second, third, or fourth receive apertures when the sample volume gate is moved toward or away from the probe.

19. The system of claim 13, wherein the processor alters a lateral position of one or more of the transmit aperture, the first receive aperture, the second receive aperture, the third receive aperture, or the fourth receive aperture within the probe when the sample volume gate is laterally moved relative to the probe.

20. The system of claim 19, wherein the processor alters the lateral position of one or more of the transmit aperture, the first receive aperture, the second receive aperture, the third receive aperture, or the fourth receive aperture without changing distances between the transmit aperture and the receive apertures.

* * * * *